(12) United States Patent
Heijl et al.

(10) Patent No.: US 6,527,391 B1
(45) Date of Patent: Mar. 4, 2003

(54) METHOD AND AN APPARATUS FOR PERFORMING A VISUAL FIELD TEST, AND COMPUTER PROGRAMS FOR PROCESSING THE RESULTS THEREOF

(76) Inventors: Anders Heijl, Biskopsgatan 22, 223 62 Lund (SE); Jonny Olsson, Bomvägen 20, 226 51 Lund (SE); Boel Bengtsson, Fru Alstad, Stengården, 231 96 Trelleborg (SE)

( * ) Notice: Subject to any disclaimer, the term of this patent is extended or adjusted under 35 U.S.C. 154(b) by 0 days.

(21) Appl. No.: 09/869,495

(22) PCT Filed: Dec. 15, 1999

(86) PCT No.: PCT/SE99/02365

§ 371 (c)(1),
(2), (4) Date: Aug. 8, 2001

(87) PCT Pub. No.: WO00/40140

PCT Pub. Date: Jul. 13, 2000

Related U.S. Application Data (60) Provisional application No. 60/114,799, filed on Jan. 4, 1999.

(30) Foreign Application Priority Data

Dec. 30, 1998 (SE) .............................................. 9804616

(51) Int. Cl.$^7$ ................................................ A61B 3/02
(52) U.S. Cl. ..................................................... 351/243
(58) Field of Search ................................ 351/222, 223, 351/224, 226, 237, 239, 212, 205, 243, 246; 600/558

(56) References Cited

U.S. PATENT DOCUMENTS

| | | | | |
|---|---|---|---|---|
| 4,927,260 A | * | 5/1990 | Gordon | ...................... 351/243 |
| 5,319,398 A | | 6/1994 | Weijland | ..................... 351/212 |
| 5,461,435 A | | 10/1995 | Rootzen et al. | ............. 351/226 |
| 5,652,640 A | * | 7/1997 | Schneider et al. | .......... 351/205 |
| 5,864,385 A | * | 1/1999 | De La Rosa | ................ 351/246 |

FOREIGN PATENT DOCUMENTS

| | | | |
|---|---|---|---|
| EP | 0363811 | 4/1990 | ........... A61B/3/024 |
| GB | 2305515 | 4/1997 | ........... A61B/3/024 |

OTHER PUBLICATIONS

"The Octopus Glaucoma G1 Program" by J. Flammer et al. Glaucoma Mar.–Apr. 1987, 9:67–72.

"Visual Fields Examination and Interpretation" Automated Perimetry in Glaucoma pp. 125, 137, and 151 (1996).

* cited by examiner

*Primary Examiner*—George Manuel (57) ABSTRACT

The invention relates to visual field tests, wherein a plurality of visual stimuli are successively presented to a test subject and the responses from the test subject are recorded in order to determine the test subject's perception of visual stimuli. With the aid of a confidence level function and the recorded responses, at least two visual field test values of different confidence levels are calculated. A result of the visual field test and an indication of the confidence thereof, which are based on the two visual field test values of each test location, are displayed to the user.

31 Claims, 5 Drawing Sheets

|    |    |    | 26 | 24 | 27 | 27 |    |    | *Optimistic* |
|----|----|----|----|----|----|----|----|----|---|
|    |    | 29 | 30 | 31 | 31 | 27 | 22 |    |   |
|    | 31 | 32 | 29 | 29 | 33 | 31 | 32 | 28 |   |
| 25 | 33 | 35 | 30 | 34 | 35 | 34 | 32 | 32 | 25 |
| 31 | 35 | 0  | 32 | 35 | 33 | 33 | 31 | 31 | 26 |
| 35 | 32 | 0  | 36 | 27 | 23 | 25 | 25 | 29 | 25 |
| 33 | 32 | 36 | 31 | 6  | 28 | 32 | 34 | 29 | 34 |
|    | 33 | 35 | 34 | 30 | 34 | 34 | 33 | 27 |   |
|    |    | 33 | 31 | 33 | 33 | 32 | 28 |    |   |
|    |    |    | *a* | 38 | 34 | 25 | 26 |    |   |

|    |    |    | 24 | 20 | 24 | 25 |    |    |   |
|----|----|----|----|----|----|----|----|----|---|
|    |    | 26 | 27 | 28 | 28 | 25 | 19 |    |   |
|    | 29 | 29 | 27 | 27 | 31 | 29 | 29 | 25 |   |
| 22 | 30 | 31 | 29 | 31 | 33 | 33 | 29 | 28 | 21 |
| 28 | 32 | 0  | 30 | 33 | 31 | 30 | 29 | 28 | 24 |
| 31 | 29 | 0  | 33 | 23 | 19 | 21 | 20 | 26 | 21 |
| 30 | 31 | 32 | 29 | -2 | 23 | 31 | 30 | 27 | 29 |
|    | 31 | 32 | 31 | 28 | 30 | 31 | 30 | 24 |   |
|    |    | 31 | 29 | 30 | 30 | 29 | 25 |    |   |
|    |    |    | *b* | 33 | 30 | 23 | 23 |    |   |

|    |    |    | 21 | 15 | 21 | 22 |    |    | *Pessimistic* |
|----|----|----|----|----|----|----|----|----|---|
|    |    | 23 | 24 | 25 | 25 | 22 | 15 |    |   |
|    | 26 | 26 | 25 | 24 | 28 | 26 | 26 | 22 |   |
| 18 | 27 | 28 | 28 | 28 | 30 | 31 | 27 | 26 | 18 |
| 26 | 29 | 0  | 27 | 30 | 28 | 28 | 26 | 25 | 20 |
| 28 | 26 | 0  | 29 | 17 | 12 | 14 | 14 | 22 | 17 |
| 27 | 29 | 28 | 28 | -8 | 17 | 29 | 27 | 24 | 25 |
|    | 28 | 29 | 28 | 25 | 27 | 28 | 27 | 21 |   |
|    |    | 28 | 27 | 27 | 27 | 26 | 22 |    |   |
| *c* |   |    | 30 | 27 | 19 | 20 |    |    |   |

Fig. 7

|    |    |    | 2  | 0  | 2  | 2  |    |    |    |
|----|----|----|----|----|----|----|----|----|----|
|    |    |    | 2  | 4  | 4  | 4  | 0  | -5 |    |
|    |    | 4  | 4  | 0  | 0  | 3  | 1  | 3  | 0  |
| -4 | 4  | 5  | 0  | 3  | 4  | 3  | 1  | 2  | -2 |
| 1  | 5  |    | 0  | 3  | 0  | 0  | -1 | 1  | -1 |
| 5  | 1  |    | 4  | -5 | -10| -8 | -7 | -2 | -3 |
| 3  | 4  | 4  | -1 | -27| -5 | 0  | 2  | -1 | 7  |
|    | 3  | 4  | 3  | -1 | 2  | 3  | 3  | -1 |    |
|    |    | 3  | 1  | 3  | 3  | 3  | 0  |    |    |
| *a* |   |    | 8  | 5  | -3 | 2  |    |    |    |

|    |    |    | -1 | -3 | -1 | -1 |    |    |    |
|----|----|----|----|----|----|----|----|----|----|
|    |    |    | 0  | -1 | 0  | 0  | -2 | -8 |    |
|    |    | 0  | 0  | -2 | -4 | 0  | -2 | -1 | -3 |
| -7 | 0  | 0  | -2 | -1 | 0  | 1  | -2 | -1 | -6 |
| -1 | 1  |    | -3 | -2 | -3 | -4 | -4 | -3 | -5 |
| 0  | -2 |    | -1 | -7 | -10| -9 | -9 | -5 | -7 |
| 0  | -1 | 0  | -3 | -35| -7 | -2 | -2 | -4 | 0  |
|    | 0  | 0  | -1 | -4 | -3 | -1 | -1 | -5 |    |
|    |    | 0  | -1 | -1 | -1 | -2 | -4 |    |    |
| *b* |   |    | 3  | 0  | -6 | -5 |    |    |    |

|    |    |    | -4 | -10| -4 | -3 |    |    |    |
|----|----|----|----|----|----|----|----|----|----|
|    |    |    | -3 | -3 | -2 | -3 | -5 | -12|    |
|    |    | -2 | -2 | -4 | -5 | -2 | -3 | -3 | -6 |
| -11| -2 | -2 | -3 | -3 | -2 | 0  | -4 | -4 | -9 |
| -4 | -1 |    | -5 | -3 | -5 | -5 | -6 | -5 | -7 |
| -2 | -4 |    | -3 | -16| -21| -19| -18| -8 | -11|
| -3 | -2 | -3 | -4 | -41| -16| -3 | -4 | -6 | -3 |
|    | -2 | -2 | -3 | -6 | -5 | -3 | -3 | -8 |    |
|    |    | -2 | -4 | -3 | -3 | -3 | -7 |    |    |
| *c* |   |    | 1  | -2 | -9 | -8 |    |    |    |

METHOD AND AN APPARATUS FOR PERFORMING A VISUAL FIELD TEST, AND COMPUTER PROGRAMS FOR PROCESSING THE RESULTS THEREOF

This application claims the benefit of Provisional Application No. 60/114,799, filed Jan. 4, 1999.

FIELD OF THE INVENTION

The present invention relates to a method and an apparatus for performing a visual field test. It also relates to computer-readable media which store a computer program for processing a result of one or more visual field tests.

BACKGROUND OF THE INVENTION

Visual field testing is one of the most important examination methods in eye care. It is used for examining the range and the sensitivity of a subject's visual field in connection with diagnosis and treatment of different diseases of the eye, e.g. glaucoma and retinal disease, and of the central nervous system, e.g. brain tumours and inflammations of the optic nerve.

Today most visual field tests are performed with the aid of special computerised instruments (the so-called perimeters) measuring the limit or threshold of a subject's perception of light at a number of test locations in the subject's visual field.

Typically, the test is performed in the following way. The patient is seated in front of a perimeter and asked to look steadily at a centrally placed fixation target, e.g. on a screen or in a hemispherical bowl. Visual stimuli are presented successively with different intensities and at different locations. The patient is asked to press a response button every time he perceives a stimulus, whether close to or distant from the fixation target, whether faint or strong. Alternatively or additionally, the perception of stimuli can be recorded by objective methods, such as measurement of electric potentials in the brain or in the eye of the patient (VER perimetry and ERG perimetry, respectively) or recording of pupil reactions (pupil perimetry).

There are different strategies for selecting test locations and intensities of the stimuli presented at these test locations in order to establish a patient's threshold for perception of light. In one common method, the so-called staircase method, a stimulus which has an intensity close to the expected threshold value at the test location concerned is shown. If the patient does not respond to the stimulus, the intensity of the subsequently presented stimuli is thereafter increased stepwise until a response is received from the patient, i.e. until a stimulus is seen. The first intensity level at which a response is received may be defined as an estimate of the threshold of the test location concerned. The precision of the test can be increased by reversing the test process when the first response is received, and by continuing it in smaller steps with decreasing intensities until the first unseen stimulus is encountered. The threshold may then again be estimated as the intensity level of the last seen stimulus. If, on the other hand, the patient responds to the first stimulus, the intensity is decreased stepwise until no response is received, whereupon the test procedure is reversed.

There are several known strategies of how to vary the intensities of the visual stimuli depending on the response to previous stimuli in order to obtain a rapid and accurate determination of the threshold value of each test location.

In order to obtain more accurate threshold estimates, responses to the visual stimuli at all test locations can also be processed by statistical methods. See e.g. U.S. Pat. No. 5,461,435, wherein the maximum of a posterior probability function is used for calculating the best estimates of the threshold values during and after the test. See also the article "Scandinavian Journal of Statistics, Vol. 21, No 4, p 375–387, 1994, Olsson J and Rootzén H", which describes another particular method of estimating the best threshold value of each test location from the estimated distribution of threshold values of each test location, namely MPM or Marginal. Posterior Mean which is achieved by calculating a mean threshold value from the posterior probability distribution of threshold values.

Figure 1:
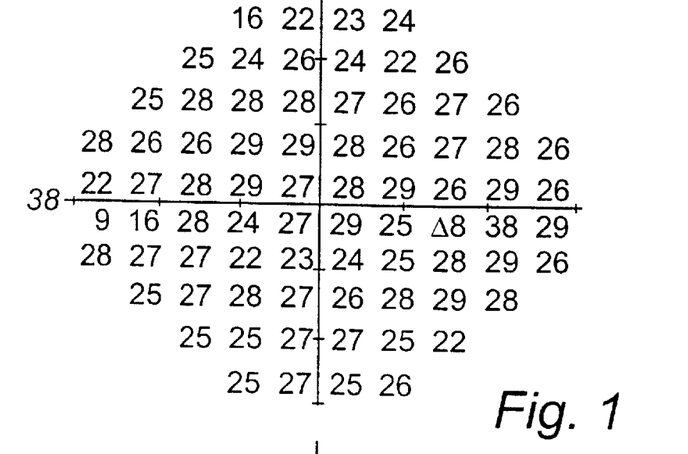
FIGS. 1–3, which have already been discussed, show different examples of visual field maps.

The geographical distribution of points showing reduced sensitivity is of great clinical importance, and it is, therefore, very important that this geographical information is displayed to the user in an easily comprehensible way. A common way of displaying the result is to show the numerical value of the single best threshold estimate at each test location in a map. An example of such a map is shown in FIG. 1. Such numerical maps are difficult to use. Greyscale representation facilitate the usage to some extent.

Figure 2:
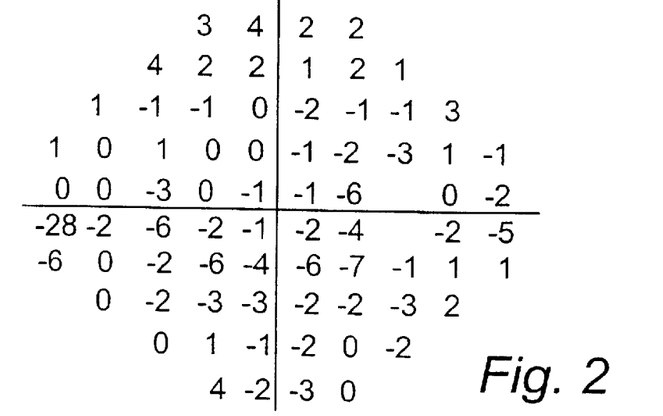
Figure 3:
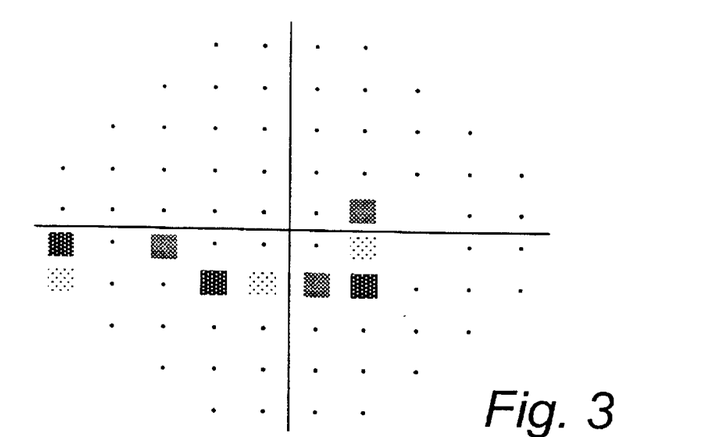

The result of the visual field test may also be shown as a deviation map that shows the deviation of each measured threshold value from the corresponding threshold value of a mean age-corrected reference field or a significance map that shows the significances of these deviations. FIGS. 2 and 3 show an example of a deviation map and a significance map, respectively. The deviation maps and the significance maps are advantageous in that they show deviations from expected normal values and the significances of such deviations.

The result of a visual field test can also be presented in the form of a so called visual field index, which may e.g. be obtained by averaging the calculated threshold values of all test location.

All test methods developed so far have been focused on obtaining one or two good estimates of the threshold value at each test location using as few visual stimuli as possible. The threshold values which represent these estimates are displayed, either directly or in refined versions, and used for assessing whether the measured visual field deviates from a normal field or not.

However, it has been established that threshold values from the same test location of the same eye, exhibit variability within a test and between tests often called short term fluctuation and long term fluctuation, respectively. In addition the estimation of the threshold value is always associated with a measurement error. This measurement error is influenced by many factors, e.g. the frequencies of false positive and false negative responses, loss of fixation and variations in stimulus response times. Therefore, a single threshold value estimate determined at a certain test location at a certain moment during the test does not give a complete representation of the patient's capability of perceiving light at that point of the visual field. Thus, there is a risk of erroneous conclusions with the present methods.

SUMMARY OF THE INVENTION

One object of the present invention is to suggest a method and an apparatus for performing a visual field test, which method and apparatus give a better representation of the visual field of the test subject.

Another object of the invention is to suggest such a method and apparatus, which process the responses received from the test subject during a visual field test such that the user obtains more information of the measured visual field, thereby facilitating the interpretation.

At least one of these objects are achieved by a method, an apparatus and computer-readable media having the features of claims 1, 15, 26, and 31, respectively.

The present invention is based on the understanding that the estimation of the threshold values is more or less certain due to estimation errors as well as short and long-term fluctuations, that the degree of confidence varies between different test locations, with normality and with disease, and that a better representation of the measured visual field would be obtained if the confidence of the test result was estimated, used in the subsequent testing and/or conveyed to the user.

In a first aspect, the present invention relates to a method of performing a visual field test, comprising the steps of successively presenting a plurality of visual stimuli to a test subject, each visual stimulus being presented at a test location; recording, for each visual stimulus, any response thereto from the subject; and calculating, on the basis of the recorded responses and with the aid of a confidence level function, at least two visual field test values of different confidence levels of the test subject's perception of visual stimuli, said at least two visual field test values being calculated on the basis of the same recorded responses.

The presentation of visual stimuli and the recording of responses thereto can be performed as in the prior art. However, the responses are processed in a new way.

More particularly, a confidence level function, $c(v)$, is used to calculate confidence levels of visual field test values, $v$, e.g. threshold value estimates, $t$. The confidence level function can be any function which is suitable for establishing values of different confidence levels of the test subject's perception of visual stimuli. Below examples of different confidence level functions are given.

A threshold value estimate $t_1$ with a certain confidence level $Kl_i$ is a solution or approximate solution to the equation $c_i(t_i)=Kl_i$ of test location i. The confidence level function may have the property of being increasing with threshold value (here denoted "increasing confidence level function") i.e.: if $t_1<t_2$, then it follows that $c_i(t_1) \leq c_i(t_2)$ (equation (a)).

The values of the confidence level function $c_i(t)$ may depend on all data recorded from the patient such as responses, fixation etc and all the data recorded on the perimeter such as stimulus levels, time of stimulus and so on. These data are denoted test data.

The confidence level function $c_i(t)$ could e.g. indicate the probability that the threshold is located in the interval $(-,t]$ i.e. equal to or smaller than t (such a probability satisfies equation (a)) or in the interval $(t,)$. Such a function is here denoted "probability type confidence level function".

An example of the threshold estimate calculations in the probability type confidence level functions is the following. Let $c_i(t_1)=Kl_i=50\%$, and assume that $c_i(t)$ is a "probability type confidence level function" indicating the probability that the threshold is in the interval $(-,t]$. In this case $t_1$ is a threshold estimate such that there is a 50% probability in the Bayesan sense that the actual threshold is below $t_1$.

A different and alternative confidence level function is the following. Compute the probability that a certain function of the test data $g_i=g_i$ (data) attains a value in the critical region $C_i$ (which may depend on the test data). If it is assumed that the patient has a patient behaviour or part of a patient behaviour which is characterised by the parameter x, this probability is denoted with $P(g_i \epsilon C_i|x)$. In general, the true value of the patient parameter is unknown and $P(g_i \epsilon C_i|x)$ is calculated for hypothetical values of x. Functions which depend on $P(g_i \epsilon C_i|x)$ are here denoted "test type confidence level function". For instance with $C_i=(t,b]$ or $(a,t]$, intervals on the real line, and x denoting a certain patient behaviour $c_{i(t)}=1-P(t<g_i \leq b|x)$ and $c_{i(t)}=P(a<g_i \leq t|x)$ are test type confidence level functions that satisfy equation a.

It is possible to calculate other confidence level function from $l_{(t)}/L$, wherein $l_{(t)}$ denotes the likelihood function, i.e. the probability of obtaining the observed test data given that the threshold is t, and L is the supremum of $l_{(t)}$ over all values of t. This is here called a "likelihood type confidence level function". In this case the confidence level may be non-increasing.

If the confidence level function is not strictly increasing then $c_{i(t)}=K_i$ may have several solutions and there are more than one threshold estimate with the same confidence level. In this case, a rule for combining the different threshold estimates is needed.

More than one confidence level function may be used at one and the same test location. It is conceivable that confidence levels $K1_i$, $K2_i$, ... are calculated using test data.

Confidence level functions may also be defined for other arguments than a single threshold, t. For instance confidence level functions, $c_i(d_i)$, expressing the confidence in a deviation, $d_i=t_i-n_i$, of a single threshold, $t_i$, from the corresponding threshold value of a mean age-corrected reference field, $n_i$. In the single test a number, N, of confidence level functions $c_i(f(t_1,t_2,\ldots,t_n))$, for i=1, ..., N, may be calculated for functions, $f(t_1,t_2,\ldots t_n)$, of thresholds from n test points (such functions are often called visual field indices). An example of a single test confidence level function is $f(t_1,t_2,\ldots,t_n)=\Sigma_{i=1}^n(t_i/n)$, the average threshold value. When analysing results from more than one visual field test, confidence level functions $c_i(\Delta_i)$ may be defined for e.g. differences, $\Delta_i=t_{i,2}-t_{i,1}$, between threshold values $t_{i,1}$ and $t_{i,2}$ of the same test point measured at a first and a second visual field tests. Another example of analyses using data from several visual field tests is, with $\beta=f(t_{1,1}, t_{2,1}, \ldots, t_{n,1}, t_{1,2}, t_{2,2}, \ldots, t_{n,2}, \ldots t_{1,m}, t_{2,m}, \ldots, t_{n,m})$ (where $t_{i,j}$ is the threshold value of test point i at visual field test j) estimating a rate of change, a confidence level, function $c_i(\beta)$ that may be used to express the confidence in $\beta$, the rate of change. Thus the use of confidence level functions also applies to functions of threshold values from one or several visual field tests. It can also be similarly applied to any visual field test value indicating the test subject's perception of visual stimuli, e.g. the gradient of the frequency-of-seeing curve.

Furthermore, perception as used in this application should be taken to include perception measured by subjective methods, e.g. pressure of a response button by the test subject, as well as perception measured by objective methods, e.g. measurement of electric potentials in the brain or in the eye of the test subject.

The two visual field test values of different confidence levels can be used internally in a test algorithm, for determining how to proceed with the current test or a later test. In a preferred embodiment the method comprises, however, the further step of displaying a result of the visual field test and an indication of the confidence thereof, said result and said indication of the confidence being based on the at least two visual field test values of different confidence levels of the test subject's perception of visual stimuli.

In a preferred embodiment, the step of calculating comprises calculating at least two visual field test values of different confidence levels for each test location. Thus at least two sets of visual field test values are obtained for the visual field of the test subject. The at least two visual field test values of a test location could be defined as two alternative results of that test location since they are calculated from the same responses.

The result of the visual field test may be given in the form of e.g. a threshold value for each test location or a visual field index as in the prior art, or in any other suitable form.

The indication of the confidence may be any indication which gives the user an idea of certainty/uncertainty of the result. It may for instance consist of at least one alternative result of the visual field test. Since the alternative results have different confidence levels, the user gets an idea of the confidence of the result from the difference between the alternative results.

The visual field test values may be values indicating the test subject's perception of visual stimuli in the whole visual field, a part of the visual field or at single test points. The visual field test values may e.g. consist of visual field indices, which are displayed as the result of the visual field test and the indication of the confidence thereof. The visual field index may be e.g. the mean value of a set of visual field test values or a distribution value, e.g. the standard deviation of a set of visual field test values.

As another alternative, the number of acceptable/unacceptable visual field test values in a set of values of a first confidence level may be determined and displayed as the result of the visual field test, whereas the number of acceptable/unacceptable visual field test values in another set of visual field test values of a second confidence level may be determined and displayed as the alternative result. Whether the visual field test value of a certain test location is acceptable or not could be determined by comparing it with a reference value.

As yet another alternative, the numerical values of the two sets of visual field test values may be displayed as the result of the visual field test and the indication of the confidence thereof. The two visual field test values at each test location, may, for instance, represent a standard estimation and a pessimistic estimation of the visual field test value. In this case the user may be reasonably sure that the test location concerned is normal if both the standard estimation and the pessimistic estimation indicate that the test location is normal.

In the currently preferred embodiment, three visual field test values which represent an optimistic, a standard and a pessimistic test result are determined.

As another example, the indication of the confidence may consist of an indication that the confidence is sufficient/insufficient. This indication can be determined e.g. by comparing the difference between the two visual field test values of each test location with a predetermined value.

The result of the visual field test may be shown in one single map, wherein the result and the indication of the confidence thereof are shown at each test location, or in several maps, where each map show e.g. the result of a predetermined confidence level. Furthermore, interpolated results may also be shown at any point between the test locations.

The visual field test values may be shown directly, either as explicit numerical values or graphically, e.g. by means of a colour or grey scale, on the map as the alternative results of the test location concerned. They may also be refined and shown, e.g. as the deviations from expected visual field test values, which are based on a statistical normal values of a population, or from other reference values. As a further alternative, the significances of the above-mentioned deviations may be shown in the maps.

A preferred way of calculating the at least two visual field test values comprises the sub-steps of calculating a plurality of visual field test values, sorting said plurality of visual field test values by size, and selecting visual field test values of predetermined ordinal numbers to be used as said at least two visual field test values. This is an advantageous way of calculating the visual field test values since it requires a limited amount of computing capacity, with negligible loss of information.

In a preferred embodiment, the visual field test value is a threshold value of the test subject's perception of visual stimuli.

The present invention is advantageous in that it gives the user and/or a computer algorithm an indication of the confidence of the test result. This is most valuable since the uncertainty of the test result may vary to a considerable extent between different patients and different tests. Knowledge of the confidence level makes it easier to determine whether the visual field is defective or not. The invention is particularly advantageous when an indication of the confidence of each different test location is determined and displayed, since the confidence of the result may present a large variability between different test locations.

In a second aspect, the invention relates to an apparatus for performing visual field test, which comprises means for successively presenting a plurality of visual stimuli to a test subject, each stimulus being presented at a test location; means for recording, for each visual stimulus, any response thereto from the subject; and, means for calculating, on the basis of the recorded responses and with the aid of a confidence level function at least two visual field test values of different confidence levels of the test subject's perception of visual stimuli, said at least two visual field test values being calculated on the basis of the same recorded responses.

The responses need not necessarily be evaluated in immediate connection with the testing of the test subject. Instead, the responses to the visual stimuli may be stored in a memory and evaluated at a later time and even in a different apparatus or computer. In a third aspect, the invention thus relates to a computer-readable medium having stored thereon a computer program for processing a result of a visual field test, according to which a plurality of visual stimuli are successively presented to a test subject, each visual stimulus being presented at a test location, and any response from the subject to a visual stimulus is recorded, said computer program comprising instructions for a general purpose computer to perform the steps of calculating on the basis of the recorded responses and with the aid of a confidence level function, at least two visual field test values of different confidence levels of the test subject's perception of visual stimuli, said at least two visual field test values being calculated on the basis of the same recorded responses.

An alternative way of evaluating the visual field test by using the knowledge of the confidence levels of different visual field test values, is to calculate the confidence levels at different test locations of a certain visual field test value. In a fourth aspect, the invention thus relates to a computer readable-medium having stored thereon a computer program for processing a result of a visual field test, according to which a plurality of visual stimuli are successively presented to a test subject, each visual stimulus being presented at a test location, and any response from the subject to a visual stimulus is recorded, said computer program comprising instructions for a general purpose computer to perform the steps of calculating on the basis of the recorded responses and with the aid of a confidence level function, the confidence level of a predetermined visual field test value at each test location; and producing a map of the plurality of test locations, wherein the confidence levels of the predetermined visual field test value is displayed for each test location.

The idea of calculating results of different confidence levels could also be used in the follow-up of visual field tests. In a fifth aspect, the invention thus relates to a computer-readable medium having stored thereon a computer program for processing a result of at least two visual field tests, according to each of which a plurality of visual stimuli are successively presented to a test subject, each visual stimulus being presented at a test location, and any response from the subject to a visual stimulus is recorded, said computer program comprising instructions for a general purpose computer to perform the steps of calculating on the basis of the recorded-responses from said at least two visual field tests and with the aid of a confidence level function, at least two results of different confidence levels for said at least two visual field tests.

By following the development of the visual field on different confidence levels, more and better information could be gained.

The apparatus and the computer programs have the same advantages as described above for the method of the present invention. Furthermore, the features discussed in connection, with the method could also be implemented in the apparatus and in the computer programs. Preferably, all method steps are performed under the control of a computer.

The above-mentioned and other objects and features of the present invention will become more apparent from a consideration of the following detailed description in conjunction with the accompanying drawings.

DESCRIPTION OF THE PREFERRED EMBODIMENT

Figure 4:
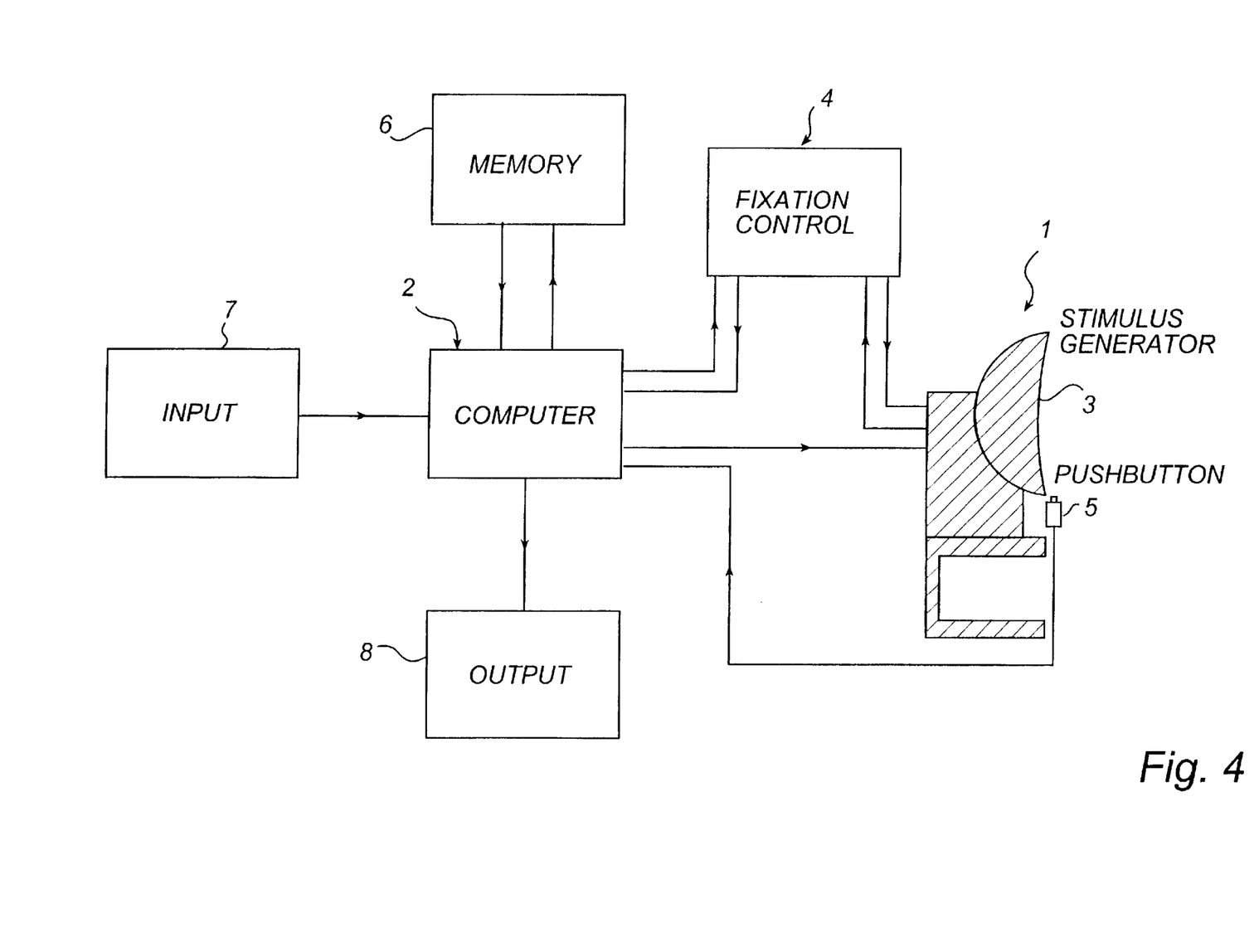
FIG. 4 schematically shows a computerised perimeter.

FIG. 4 shows schematically, partly in the form of a block diagram, the design of a computerised perimeter, by means of which the method of the invention can be carried out. The perimeter consists essentially of a stimulus generator 1 and a computer 2 for controlling the generator and for assessing the responses to presented stimuli that are received from the patient.

The stimulus generator 1 has a screen 3, which may be hemispherical or have some other suitable shape, and in front of which the patient is seated. The screen is provided with a fixation target, for example in the form of a light emitting diode at which the patient is asked to look throughout the test. The stimulus generator 1 serves to successively present well-defined visual stimuli at selected test locations on the screen, which should be evenly illuminated. These stimuli can be generated by means of a projection system or by means of fixed light sources (light-emitting diodes or optical fibres) or by any other suitable means.

Advantageously, the perimeter also has means 4 for monitoring the patient's fixation of the fixation target, such that stimuli presented when the patient is blinking or does not maintain fixation can be sorted out or repeated. The fixation monitoring function may be implemented electronically or with the aid of a TV camera. Other types of fixation monitoring are of course also possible.

The perimeter further comprises a press button 5, by means of which the patient should give a response each time he perceives a visual stimulus on the screen. Responses may also be obtained by measuring pupillary responses or visually evoked potentials or by any other suitable means. The press button 5 is connected to the computer 2 which for each visual stimulus records any response thereto from the subject. The computer 2 furthermore assesses every response from the patient and, on the basis thereof, determines the location and the intensity of the next visual stimulus in compliance with a control program stored in the computer. The computer has a memory 6, in which for example responses to the stimuli are stored. The computer is also provided with an input unit 7, by means of which an operator can supply information to the perimeter and an output unit 8, by means of which the results of the visual field tests are presented. The input unit 7 may, for instance, consist of a keyboard and the output unit 8 of a printer or a display device which make the result of the test and the confidence thereof available to the user.

The physical design of the perimeter described above does not differ from that of the prior-art perimeters. As will be explained hereinafter, the perimeter of the invention, however, processes and displays the result of the visual field test in a new manner with the aid of a new program in the computer.

When the presentation of visual stimuli is completed, the visual field test values, which in this example are threshold values, of all test locations are calculated on the basis of the responses (both positive and negative responses) by the computer program of the computer 2. In this example three threshold estimates (pessimistic/standard/optimistic) of different confidence levels are produced with the aid of a probability type confidence level function, namely the posterior probability function.

As is well-known, a posterior probability function is a product of a prior probability function and the likelihood function.

The prior probability function indicates a priori known information about a parameter which is to be estimated. In this case, the prior probability function specifies how common different threshold values are in a specific population of subjects.

The likelihood function indicates the probability of obtaining a specific set of values in a sample of a random variable, the distribution of which depends on an unknown parameter. In this case, the likelihood function specifies the probability of obtaining a specific series of responses (seen stimulus/unseen stimulus) for a specific series of stimulus intensities, the unknown parameter being the threshold value.

The posterior probability function may be used to estimate the threshold values. One possibility of doing this is to find the threshold values which maximise the posterior probability function and to use these as threshold estimates.

However, in the preferred embodiment a distribution of threshold values is instead estimated for each test location with the aid of the posterior probability function. The estimated distribution of threshold values consists at each test location, e.g. at test location i, of a sequence of N threshold values $(t_{i1}, t_{i2}, \ldots t_{iN})$. Each sequence is then used to calculate three threshold values of different confidence levels.

More particularly, a conditional posterior probability function is used for the calculation of the threshold values. A conditional posterior probability function is a posterior probability function of the parameters of one test location, given the parameters of all other test locations. It can be expressed as:

$$g_i(s_i,t_i)=l_i(t_i)p_i(s_i)f_i(s_i,t_i) \quad (1)$$

where $g_i$ is the conditional posterior probability of test location i, $t_i$ is the threshold value of test location i and $s_i$ is the defect status variable, which can be +1 or −1, of test location i. The defect status indicates whether the test location is a normal test location (+1) or a defective test location (−1). Furthermore, $l_i(t_i)$ in formula (1) is the likelihood function of test location i, which can be expressed as:

$$l_i(t_i) = \left\{ \prod_{q=1;\text{response}}^{N_i} \left( FP + (1-FN-FP)\Phi\left(\frac{-d_q+t_i}{Sd_i}\right)\right) \times \prod_{q=1;\text{no response}}^{N_i} \left( 1-FP-(1-FN-FP)\Phi\left(\frac{-d_q+t_i}{Sd_i}\right)\right) \right\} \quad (2)$$

where FP is the frequency of false positive responses (the patient responds despite having not seen a stimulus), FN the frequency of false negative responses (the patient does not respond despite having seen the stimulus), $N_i$ the number of stimuli presented at the i:th point, $d_q$=the q:th stimulus intensity, $\phi$ is the standard normal distribution function and $Sd_i$ is the standard deviation at the i:th test location.

Furthermore, $p_i(s_i)$ in formula (1) is the conditional prior defect status probability of test location i, which is expressed as $$p_i(s_i) = \exp\left\{ s_i\left( \sum_{j \in n_i^s} \beta_{i,j}s_j \right)/2 \right\} \quad (3)$$

where $n_i^s$ is the number of nearest neighbours regarding defect status to test locations i and $\beta_{ij}$ is a parameter which measures the dependence between test locations i and j.

Moreover, $f_i(s_i,t_i)$ in formula (1) is the conditional prior density of the threshold values and can be expressed as $$f_i(s_i, t_i) = \frac{1}{\sigma_i(s_i)\sqrt{2\pi}} \exp\left\{ -\frac{1}{2\sigma_i^2(s_i)}(t_i - \mu_i(s_i) - c\sigma(s_i)\overline{d}_i(s))^2 \right\} \quad (4)$$

where c is a constant. Moreover, $\mu_i(s_i)$ is either $\mu_i(+1)$ or $\mu_i(-1)$. $\mu_i(+1)$ is the normal age-corrected threshold value of test location i and $\mu_i(-1)$ is the defective age-corrected threshold value thereof. Furthermore, $d_i(s)$ is the mean value of the standardised deviations of the neighbouring test locations.

Figure 5:
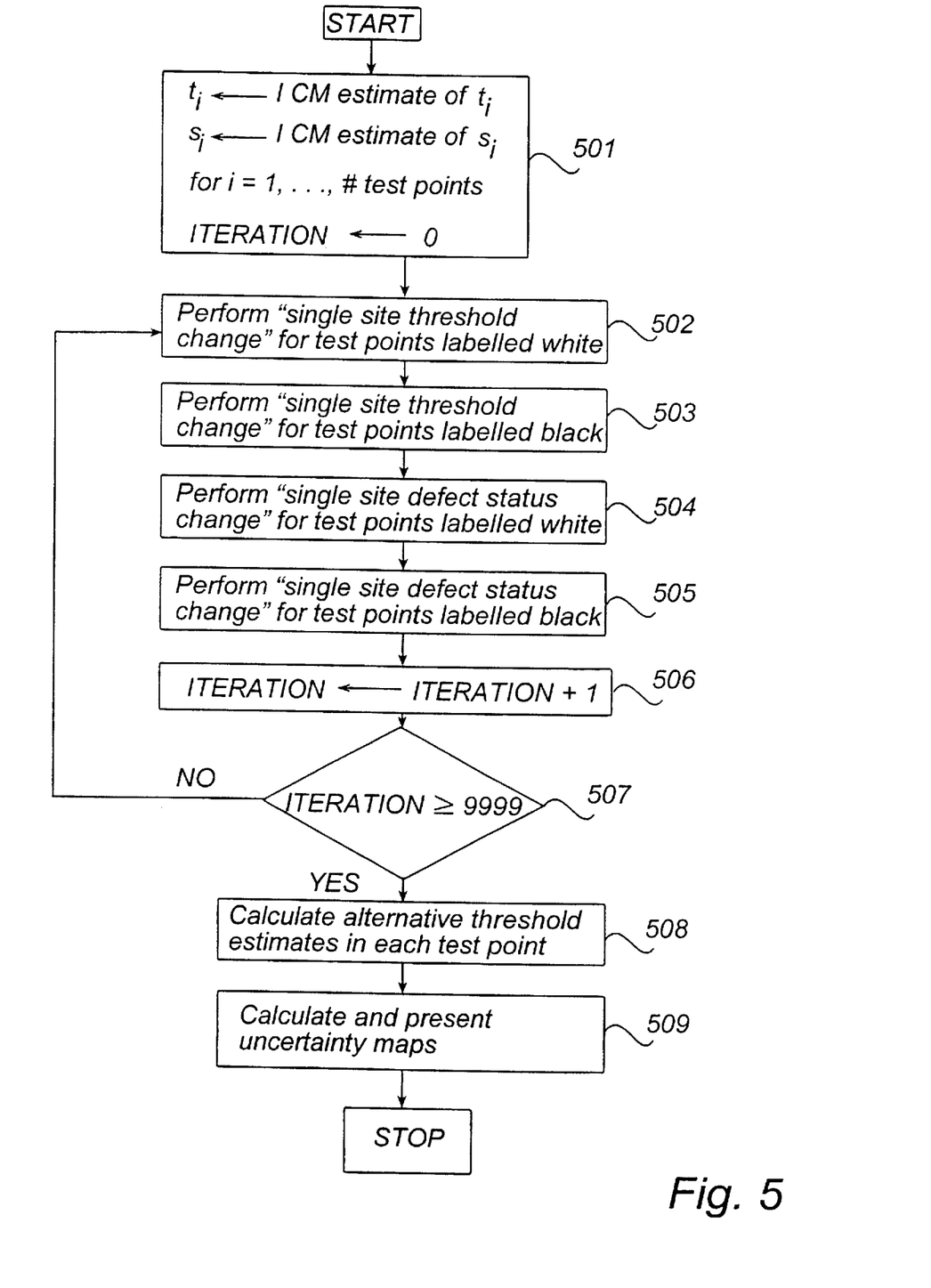
FIG. 5 is a flow diagram-of one way of performing a visual field test according to the present invention.

First at each test location the threshold values and the defect status value is initiated to the ICM estimates (step 501), computed as described in U.S. Pat. No. 5,461,435.

Then a sequence of threshold values is generated at each test location, as described in Scandinavian Journal of Statistics, Vol. 21, No 4, p 375–387, 1994, Olsson J and Rootzén H. This technique of generating sequences of threshold values and defect status values are known as Markov Chain Monte-Carlo, a well-known method for exploiting posterior probabilities.

The test locations are partitioned into black and white test locations, by labelling first one test location white and then each test location which is situated diagonally next to any white test location as white and all other test locations as black.

First the method visits all the white test locations in order, row by row, and performs a single site threshold change in each test location (step 502). A "single site threshold change-" consists of the following: The single site threshold change simulation of a new value for $t_i$ consists of first taking a random number with normal distribution $T_i$, mean $\mu_i(s_i)+c\sigma(s_i)d_i(s)$, and variance $\sigma^2_i(s_i)$, and then to accept it and let it replace ti with probability $l_i(T_i)/\max_t l_{i(t)}$, and to repeat the procedure if it is not accepted. Here $\max_t l_{i(t)}$ has to be computed numerically. However, if e.g. the expected value of $T_i$ is far from that value of $t_i$ which maximises $l_{i(t)}$ rejections may be too frequent. Hence, whenever the number of rejections exceeds a predetermined number the method of generating $t_i$ is changed and, $l_i(t_i)f_i(s_i,t_i)$ is calculated for a grid of discrete values of $t_i$ and uniform random numbers are used to select $T_i$. The use of $\max_t l_{i(t)}$ and the second method for generating $T_i$ significantly reduce the computation time as compared to a straightforward rejection method.

Subsequently, the method visits all the black test locations in order, row by row, and performs a single site threshold change in each test location (step 503). Together the visits with single site threshold changes in white and black locations are labelled a threshold scan (steps 502 and 503). After each threshold scan the threshold of each test location is stored in memory.

The method then visits all the white test locations in order, row by row, and performing a single site defect status change at each test location (step 504). A "single site defect status change" consists of the following: In the single site defect status change simulation $s_i$ is set equal to 1 with probability $$\frac{f_i(1,t_i)p_i(1)}{f_i(-1,t_i)p_i(-1)+f_i(1,t_i)p_i(1)} \quad (5)$$

and otherwise $s_i$ is set to −1.

Subsequently, the method visits all the black test locations in order, row by row, and performs a single site defect status change at each test locations (step 505). Together the visits with single site defect status changes at white and black locations are labelled a defect status scan (steps 504 and 505).

The sequence of a threshold scan and a defect status scan is then iterated n=9999 times. After each iteration, an iteration variable is incremented by 1 (step 506), whereupon the method checks whether the value of the iteration variable is larger than or equal to 9999 (step 507). If this is not the case the iteration is continued, otherwise the resulting threshold values are calculated as follow.

At test point i a sequence of threshold values ($t_{i,1}, t_{i,2}, \ldots t_{i,9999}$) has been generated. The threshold estimates that are to be presented as the result of the test are calculated by first sorting the threshold values $t_{i,1}, t_{i,2}, \ldots t_{i,9999}$ by size. Then the pessimistic threshold estimate is determined as the 500th value from the bottom, the "standard" estimate as the 5000th value (the median) and the optimistic estimate as the 9500th value from the bottom (step 508).

As an alternative to the median, the Marginal Posterior Mean, which is achieved by calculating the average $(\Sigma t_i)/9999$, could be used as the "standard" estimate. See "Scandinavian Journal of Statistics, Vol. 21, No 4, p 375–387, 1994, Olsson J and Rootzén H".

Finally the three alternative threshold estimates of each test location are used for producing confidence maps (step 509). The maps can be produced in the form of hard copies or in electronic form and presented to the user by the computer's 2 output unit 8

Figures 6, 7:
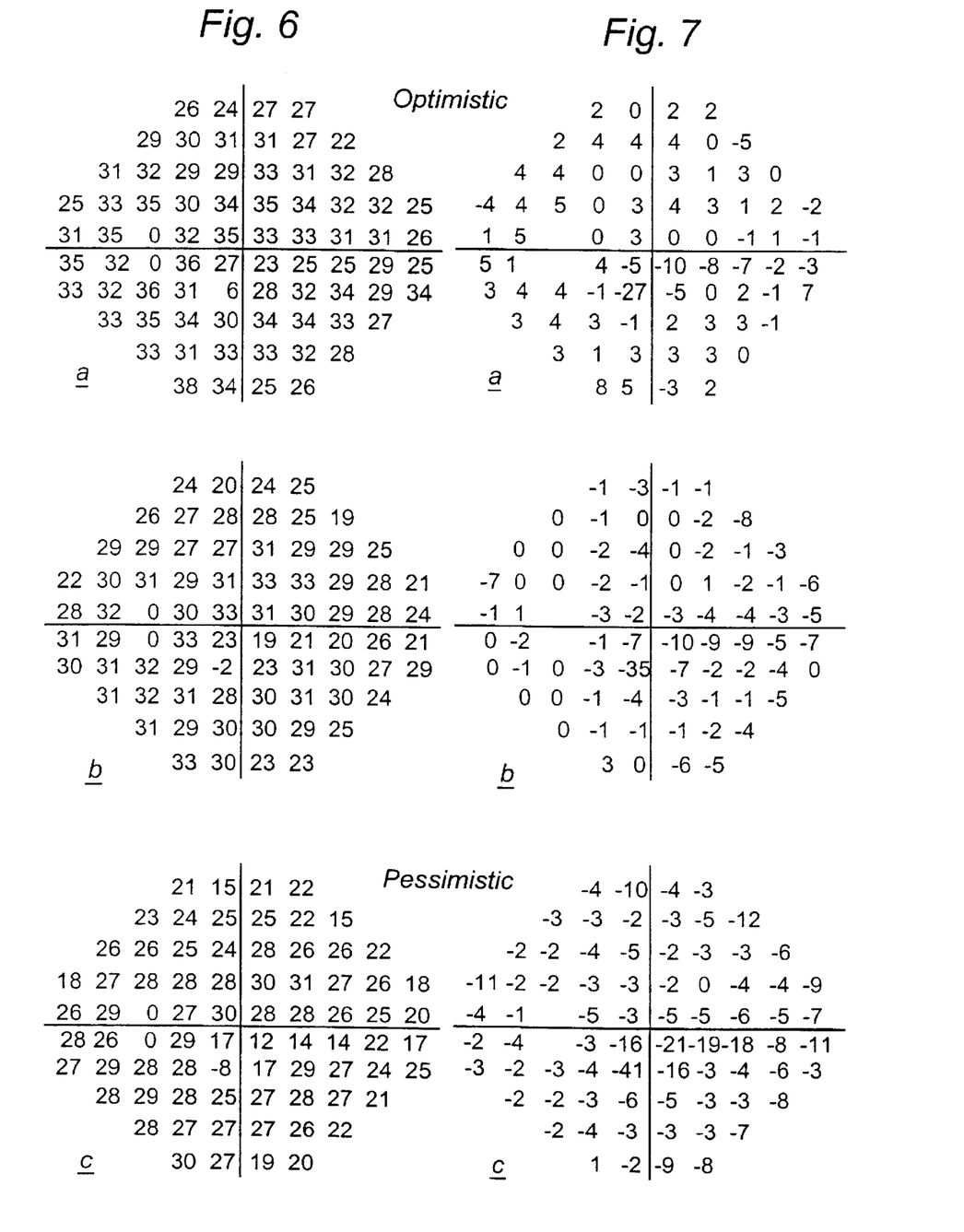
FIGS. 6a–c, 7a–c and 8 show examples of visual field maps which may be used for presenting the result of a visual field test according to the present, invention.

FIGS. 6a–c show three maps, which for each test location numerically display the optimistic estimate, the standard estimate and the pessimistic estimate, respectively of the threshold value. As an alternative, the threshold values may be presented by grey-scale representations. The different maps thus provide the indication of the confidence.

FIGS. 7a–c show three other maps, which display the alternative deviations of each threshold value from the expected value for the standard threshold estimate. As an alternative, this map can display the deviation from the expected value of the particular type of threshold estimate, e.g. the deviation of the pessimistic estimate from the expected value of a pessimistic threshold estimate.

Figure 8:
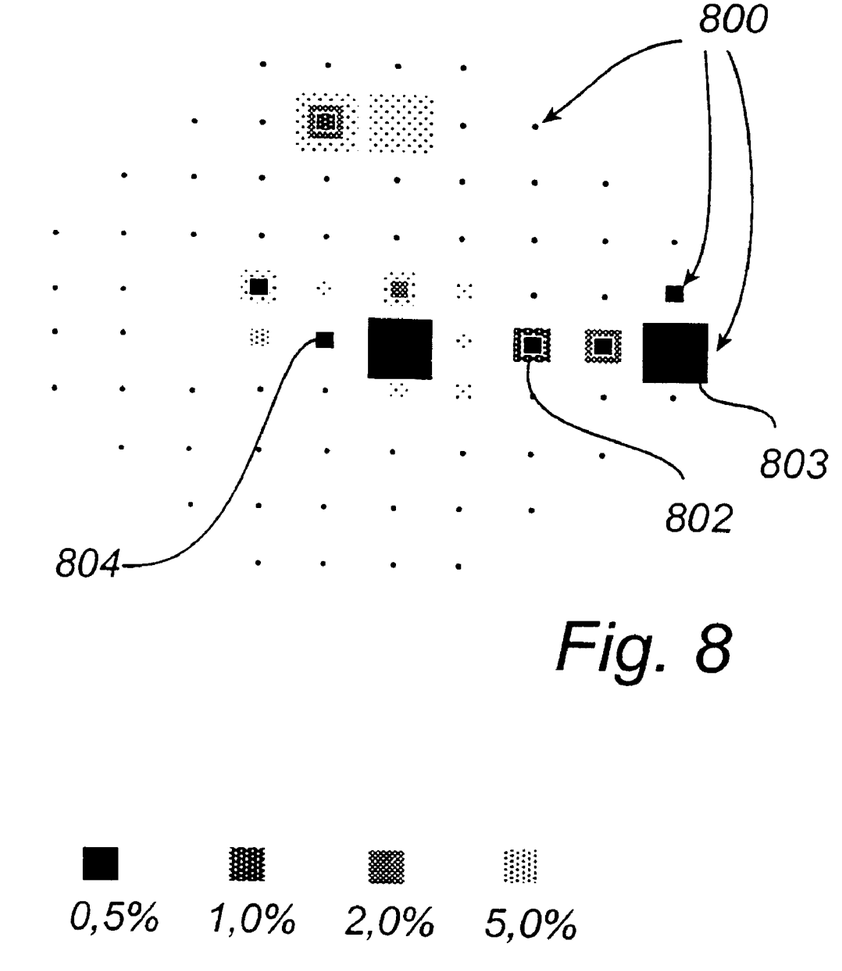

FIG. 8 shows still another map, which displays by grey-scale representation the significances of the alternative deviations from a normal value. Each dot 800 represents a test location. The test locations where the threshold value deviate significantly from the normal value are marked with squares of different sizes. The darker the square, the more significant the deviation. The smallest square 801 represents the pessimistic estimate, the middle-sized square 802 the standard estimate and the largest square 803 the optimistic estimate. From this map it is evident that the confidence of the threshold value is not large at certain test locations. E.g. a test location 804 which seems to be normal when using a standard estimate, appears to be defective when using a pessimistic estimate. In this map the result of the visual field test thus consists of the different significances of the deviations and the indication of the confidence is provided by the alternative results of each test location.

It should be mentioned that all calculations described above are carried out by the computer 2.

The currently preferred embodiment of the invention has been described in the foregoing. Many modifications are however conceivable within the scope of the appended claims.

The method according to the invention is not restricted to be used together with any particular method of visual field testing, but can be applied with data collected by any such method, e.g. staircase methods, MOBS, Robbins-Monroe or even visual field screening tests.

The method according to the invention may, but need not necessarily, be used for all the test locations.

In the preferred embodiment a probability type confidence level function is used. It is also possible to use other confidence level functions. Furthermore, other types of prior probability functions may be used. For example, one may choose to have a prior probability function identically equal to 1. It is also conceivable to use other types of likelihood functions. The normal distribution function can be replaced with a logistic distribution function or any other distribution function. The likelihood function may also have a more complicated form than a product, e.g. if the responses are dependent. Different likelihood functions may be used for pessimistic/standard/optimistic visual field test values, e.g. by defining thresholds as 50% probability of seen, 20% probability of seen and so on.

The method according to the invention is not restricted to producing two or three alternative visual field test values. Any number of alternative visual field test values (at any degree of "optimism/pessimism") may be used.

The uncertainty of patient parameters may be accounted for, e.g. by using population based prior distributions of false positive and false negative responses.

What is claimed is:

1. A method of performing a visual field test, comprising the steps of successively presenting a plurality of visual stimuli to a test subject, each visual stimulus being presented at a test location, recording, for each visual stimulus, any response thereto from the subject; and calculating on the basis of the recorded responses and with the aid of a confidence level function, at least two visual field test values of different confidence levels of the test subject's perception of visual stimuli, said at least two visual field test values being calculated on the basis of the same recorded responses and for one and the same test location.

2. The method according to claim 1, further comprising the step of displaying a result of the visual field test and an indication of the confidence thereof, said result and said indication of the confidence being based on the at least two visual field test values of different confidence levels of the test subject's perception of visual stimuli.

3. The method according to claim 2, wherein the step of displaying comprises displaying at least one alternative result of the visual field test as the indication of the confidence thereof.

4. The method according to claim 2, wherein the step of calculating comprises calculating at least two visual field test values for each one of a plurality of test locations and further comprising the step of determining, for each different confidence level and for each one of said plurality of test locations, whether the corresponding visual field test value is acceptable or not, wherein the step of displaying comprises displaying an indication of the number of acceptable test locations for each different confidence level as the result of the visual field test and the indication of the confidence thereof.

5. The method according to claim 2, wherein the step of displaying comprises displaying the numerical values of said at least two visual field test values as the result of the visual field test and the indication of the confidence thereof.

6. The method according to claim 2, wherein the step of calculating comprises calculating at least two visual field test values for each one of a plurality of test locations and further comprising the step of calculating, for each test location, the deviations of said at least two visual field test values from an expected visual field test value, which is based on a statistical normal value of a population, and wherein the step of displaying comprises displaying the calculated deviation of said two visual field test values from the expected visual field test value as the result of the visual field test and the indication of the confidence thereof.

7. The method according to claim 2, wherein the step of calculating comprises calculating at least two visual field test values for each one of a plurality of test locations and further comprising the step of calculating, for each test location, the deviations of said at least two visual field test values from an expected value, which is based on a statistical normal value of a population, as well as the significances thereof, and wherein the step of displaying comprises displaying the calculated significances of said deviations as the result of the visual field test and the indication of the confidence thereof.

8. The method according to claim 1, wherein the step of calculating comprises calculating at least two visual field test values for each one of a plurality of test locations.

9. The method according to claim 8, wherein the step of displaying comprises producing at least one map of said plurality of test locations, wherein, for each test location, the result of the visual field test for that test location and the indication of the confidence thereof are displayed.

10. The method according to claim 1, wherein the confidence level function is selected from the group of an increasing confidence level function, a probability type confidence level function, a test type confidence level function and a likelihood type confidence level function.

11. The method according to claim 1, wherein the step of calculating at least two visual field test values comprises the sub-steps of
calculating a plurality of visual field test values;
sorting said plurality of visual field test values by size; and
selecting visual field test values of predetermined ordinal numbers to be used as said at least two visual field test values.

12. The method according to claim 1, wherein the step of calculating at least two visual field test values consists of calculating three visual field test values of different confidence levels which represent a pessimistic, a standard and an optimistic result, respectively.

13. The method according to claim 1, wherein the visual field value is a threshold value of the test subject's perception of visual stimuli.

14. An apparatus for performing a visual field test, comprising
means for successively presenting a plurality of visual stimuli to a test subject, each stimulus being presented at a test location;
means for recording, for each visual stimulus, any response thereto from the subject; and
means for calculating on the basis of the recorded responses with the aid of a confidence level function, at least two visual field test values of different confidence levels of the test subject's perception of visual stimuli, said at least two visual field test values being calculated on the basis of the same recorded responses and for one and the same test location.

15. The apparatus according to claim 14, further comprising means for displaying a result of the visual field test and an indication of the confidence thereof, said result and said indication of the confidence being based on said at least two visual field test values of different confidence levels of the test subject's perception of visual stimuli.

16. The apparatus according to claim 15, wherein the means for calculating are arranged to calculate at least two visual field test values of different confidence levels for each one of a plurality of test locations and wherein the means for displaying comprises means for producing at least one map of said plurality of test locations, wherein, for each test location, the result of the visual field test for that test location and the confidence thereof are displayed, so that a user of the map gets an indication of the confidence of the result at each of the test locations.

17. The apparatus according to claim 15, wherein the indication of the confidence comprises at least one alternative result of the visual field test.

18. The apparatus according to claim 15, wherein the means for displaying are arranged to display the numerical values of said at least two visual field test values as the result of the visual field test and the indication of the confidence thereof.

19. The apparatus according to claim 15, wherein the means for displaying are arranged to display the result of the visual field test and the indication of the confidence thereof by graphical symbols.

20. The apparatus according to claim 15, wherein the means for calculating are arranged to calculate at least two visual field test values of different confidence levels for each one of a plurality of test locations and to calculate, for each test location, the deviations of said at least two visual field test values from an expected visual field test value, which is based on a statistical normal value of a population, and wherein the means for displaying are arranged to display the calculated deviation of said two visual field test values from the expected visual field test value as the result of the visual field test and the indication of the confidence thereof.

21. The apparatus according to claim 15, wherein the means for calculating are arranged to calculate at least two visual field test values of different confidence levels for each one of a plurality of test locations and to calculate, for each test location, the deviations of said at least two visual field test values from an expected visual field test value, which is based on a statistical normal value of a population, as well as the significances of the deviations, and wherein the means for displaying are arranged to display the calculated significances of said deviations as the result of the visual field test and the indication of the confidence thereof.

22. The apparatus according to claim 15, wherein the means for calculating are arranged to calculate three visual field test values of different confidence levels which represent a pessimistic, a standard and an optimistic test result, respectively.

23. The apparatus according to claim 14, wherein the means for calculating are arranged to
calculate a plurality of visual field test values,
sort said plurality of visual field test values by size; and
select visual field test values of predetermined ordinal numbers to be used as said at least two visual field test values.

24. The apparatus according to claim 14, wherein said means for successively presenting comprises a screen, on which said visual stimuli are presented, as well as a stimulus generator for generating said visual stimuli, wherein said means for recording the responses comprises a memory, in which said responses are stored, and wherein said means for calculating comprises a data processor, which moreover is arranged to control the operation of the means for presenting, the means for recording and the means for displaying.

25. A computer-readable medium having stored thereon a computer program for processing a result of a visual field test, according to which a plurality of visual stimuli are successively presented to a test subject, each visual stimulus being presented at a test location, and any response from the subject to a visual stimulus is recorded, said computer program comprising instructions for a general purpose computer to perform the steps of
calculating on the basis of the recorded responses and with the aid of a confidence level function, at least two visual field test values of different confidence levels of the test subject's perception of visual stimuli, said at least two visual field test values being calculated on the basis of the same recorded responses and for one and the same test location.

26. The computer-readable memory according to claim 25, wherein said computer program further comprises instructions for the general purpose computer to perform the step of displaying the result of the visual field test and an indication of the confidence thereof, said result and said indication of the confidence being based on said at least two visual field test values of different confidence levels of the test subject's perception of visual stimuli.

27. The computer-readable medium according to claim 26, wherein the step of calculating comprises calculating at-least two visual field test values of different confidence levels for each one of a plurality of test locations and wherein the step of displaying comprises producing at least one map of said plurality of test locations, wherein, for each test location, the result of the visual field test for that test location and the confidence thereof are displayed, so that a user of the map gets an indication of the confidence of the result at each of the test locations.

28. The computer-readable medium according to claim 25, wherein the confidence level function is selected from the group of an increasing confidence level function, a probability type confidence level function, a test type confidence level function and a likelihood type confidence level function.

29. The computer-readable medium according to claim 25, wherein the step of calculating at least two visual field test values comprises the sub-steps of calculating a plurality of visual field test values;

sorting said plurality of visual field test values by size; and selecting visual field test values of predetermined ordinal numbers to be used as said at least two threshold values.

30. A computer readable-medium having stored thereon a computer program for processing a result of a visual field test, according to which a plurality of visual stimuli are successively presented to a test subject, each visual stimulus being presented at a test location, and any response from the subject to a visual stimulus is recorded, said computer program comprising instructions for a general purpose computer to perform the steps of calculating on the basis of the recorded responses and with the aid of a confidence level function, the confidence levels of a predetermined visual field test value at each test location; and producing a map of the plurality of test locations, wherein the confidence level of the predetermined threshold value is displayed for each test location.

31. A computer-readable medium having stored thereon a computer program for processing a result of at least two visual field tests, according to each of which a plurality of visual stimuli are successively presented to a test subject, each visual stimulus being presented at a test location, and any response from the subject to a visual stimulus is recorded, said computer program comprising instructions for a general purpose computer to perform the steps of calculating on the basis of the recorded responses from said at least two visual field tests and with the aid of a confidence level function, at least two results of different confidence levels for each one of a plurality of test locations for said at least two visual field tests.

* * * * *